United States Patent [19]
Kroll et al.

[11] Patent Number: 5,741,303
[45] Date of Patent: Apr. 21, 1998

[54] ELECTRODE BACK-CHARGING PRE-TREATMENT SYSTEM FOR AN IMPLANTABLE CARDIOVERTER DEFIBRILLATOR

[76] Inventors: Mark W. Kroll, 651 Carnellon Ct., Simi Valley, Calif. 93065; Kai Kroll, 5217 W. Mill Rd., Minnetonka, Minn. 55345

[21] Appl. No.: 523,718

[22] Filed: Sep. 5, 1995

Related U.S. Application Data

[63] Continuation of Ser. No. 119,487, Sep. 13, 1993, abandoned.
[51] Int. Cl.$^6$ ................................................ A61N 1/39
[52] U.S. Cl. .................................................... 607/5
[58] Field of Search ........................................ 607/5, 7

[56] References Cited

U.S. PATENT DOCUMENTS

| | | | |
|---|---|---|---|
| 5,334,219 | 8/1994 | Kroll | 607/5 |
| 5,346,506 | 9/1994 | Mower et al. | 607/7 |
| 5,366,484 | 11/1994 | Kroll | 607/5 |
| 5,395,394 | 3/1995 | Cameron | 607/5 |

*Primary Examiner*—William E. Kamm
*Attorney, Agent, or Firm*—Brad D. Pedersen

[57] ABSTRACT

An implantable cardioverter defibrillator (ICD) apparatus produces a capacitive-discharge cardioversion/defibrillation countershock to be delivered through defibrillation electrodes adapted to be implanted in a human patient. The ICD apparatus is a self-contained human implantable device including a pulse-generating capacitor system, a battery system, a sensing system, and a control system. In response to a detected cardiac dysrhythmia, the ICD apparatus selectively charges and discharges the capacitor system through the defibrillation electrodes to generate the capacitive-discharge cardioversion/defibrillation countershock. Circuitry is added to the ICD apparatus to deliver a back-charging pretreatment pulse to the defibrillation electrodes immediately prior to delivery of the cardioversion/defibrillation countershock. The back-charging pretreatment pulse is a low-energy pulse having a polarity opposite from an initial polarity of the cardioversion/defibrillation countershock. By delivering the back-charging pretreatment pulse, an inter-electrode impedance of the defibrillation electrodes is reduced and a current of the cardioversion/defibrillation countershock is increased. The voltage multiplier and second switch system deliver a low voltage back charging charge of a polarity opposite to that of the defibrillation pulse to the electrodes.

6 Claims, 6 Drawing Sheets

ELECTRODE BACK-CHARGING PRE-TREATMENT SYSTEM FOR AN IMPLANTABLE CARDIOVERTER DEFIBRILLATOR

CROSS-REFERENCE TO RELATED APPLICATION

This application is a continuation of application Ser. No. 08/119,487, filed Sep. 13, 1993, now abandoned.

BACKGROUND OF THE INVENTION

1. Field of the Invention

This invention relates to medical therapeutic apparatus and methods and more particularly to a cardioverter defibrillator apparatus and method for use in treating heart patients. The present invention provides an implantable cardioverter defibrillator apparatus which is compact and which delivers effective cardioverting or defibrillating shock energy to a patient utilizing a minimally sized charge storage element by minimizing electrode resistance in the circuit path between the apparatus and the patient's heart.

2. Background Information

The implantable cardioverter defibrillator (ICD) is a well recognized and important tool for managing the health of patients who have a history of heart problems. The typical ICD basically comprises a sealed, canister-like main unit or housing which is implanted in the patient's body and contains various electronic components, and a unitary lead/electrode apparatus which extends from the canister through the vascular system of the patient to the heart. Although many advances have been made in ICD technology over the past several years, a remaining goal is to develop a smaller apparatus without sacrificing reliability. A smaller apparatus has obvious advantages in terms of patient comfort, ease of implantation, implantation location restrictions and other factors.

Defibrillation of the human heart is effected by passing a large current through the heart for a time period of several milliseconds. A voltage is generated in the ICD canister and transmitted to the heart through the lead and electrodes. It is known that the required energy per pulse is proportional to the electrode resistance. This in turn implies that the size of the ICD device is a linear function of the electrode resistance. Accordingly, in order to accomplish the goal of minimizing the size of the ICD while maintaining shock effectiveness, it is of extreme importance to keep the electrode resistance as low as possible.

Various devices and/or methods have been used or proposed in the past for cardioversion and/or defibrillation purposes. While it is known to construct the electrodes used to deliver cardioversion and defibrillation countershocks in such a manner as to minimize inter-electrode resistance, to date this has been the only practical way in which electrode resistance has been reduced during delivery of cardioversion and defibrillation countershocks.

The concept of reducing the inter-electrode resistance by altering the waveform that is being delivered is proposed in U.S. Pat. No. 4,768,512. In this patent, a high frequency chopped waveform is applied to the electrodes in an effort to reduce a gaseous build-up at the electrodes which has the effect of increasing inter-electrode resistance. Unfortunately, the clinical effectiveness of such a high frequency, chopped waveform has not been established, and the use of this kind of alternate waveform has not gained general acceptance in the medical community.

Another concept for improving the efficacy of defibrillation countershocks is described in U.S. Pat. No. 5,314,448. In this patent, a pretreatment pulse (either a single low voltage pulse or a train of smaller pulses) are applied to the heart prior to delivery of a conventional defibrillation countershock. The objective of these smaller pretreatment pulses is to precondition the cardiac tissue so as to make the tissue near the electrodes more susceptible to capture by a subsequent larger defibrillation countershock. There is no discussion or suggestion in this patent, however, that these kind of pretreatment pulses would have any impact on the inter-electrode resistance While numerous proposals have been made to improve the effectiveness of cardioversion and defibrillation countershocks delivered by implantable cardioverter defibrillator systems, it would be desirable to provide a way in which the inter-electrode resistance could be decreased during delivery of cardioversion and defibrillation countershocks without fundamentally altering the waveforms which are accepted as effective for cardioversion and defibrillation.

SUMMARY OF THE INVENTION

The present invention is an improved implantable cardioverter defibrillator (ICD) apparatus for producing a capacitive-discharge cardioversion/defibrillation countershock to be delivered through defibrillation electrodes adapted to be implanted in a human patient. The ICD apparatus is a self-contained human implantable device including a pulse-generating capacitor system that stores an electrical charge, a battery system that internally charges the capacitor system, a sensing system that senses cardiac activity of the human patient and detects cardiac dysrythmias, and a control system which, in response to a detected cardiac dysrhythmia, selectively charges and discharges the capacitor system through the defibrillation electrodes to generate the capacitive-discharge cardioversion/defibrillation countershock. The improvement of the present invention is the addition of circuitry to deliver a back-charging pretreatment pulse to the defibrillation electrodes immediately prior to delivery of the cardioversion/defibrillation countershock. The back-charging pretreatment pulse is a low-energy pulse having a polarity opposite from an initial polarity of the cardioversion/defibrillation countershock. By delivering the back-charging pretreatment pulse, an inter-electrode impedance of the defibrillation electrodes is reduced and a current of the cardioversion/defibrillation countershock is increased.

In a preferred embodiment, the circuitry to deliver the back-charging pretreatment pulse includes a voltage multiplier connected to the battery system, a switching system connected between the voltage multiplier and the defibrillation electrodes, and a voltage rectifier connected between the switching system and the defibrillation electrodes. In an alternate embodiment particularly suitable for treatment of ventricular tachyarrhythmias, the back-charging pretreatment pulses are delivered as a series of pulses, each pulse being delivered in response to a detected R-wave so as to minimize any possibility of inducing fibrillation by delivery of the back-charging pretreatment pulses.

Accordingly, it is an object of the present invention to provide an implantable cardioverter defibrillator which reliably provides effective defibrillating shocks and which is compact for patient comfort, ease of implantation, and which is implantable in a maximum number of locations in the human body as determined by the implanting physician. A further object of this invention is to provide an apparatus which utilizes a relatively small charge storage mechanism or mechanisms which is able to deliver effective defibrillating shocks. Another object of this invention is to provide an apparatus which minimizes electrode path impedance, by back charging the electrodes, to provide maximum shock energy for a given stored charge. A final object of this invention is to provide an apparatus and method which is reliable, safe, compact (in the case of the apparatus), and which otherwise overcome the limitations and shortcomings of the prior art.

The benefits of this invention will become clear from the following description by reference to the drawings.

DESCRIPTION OF THE PREFERRED EMBODIMENT

Figure 1:
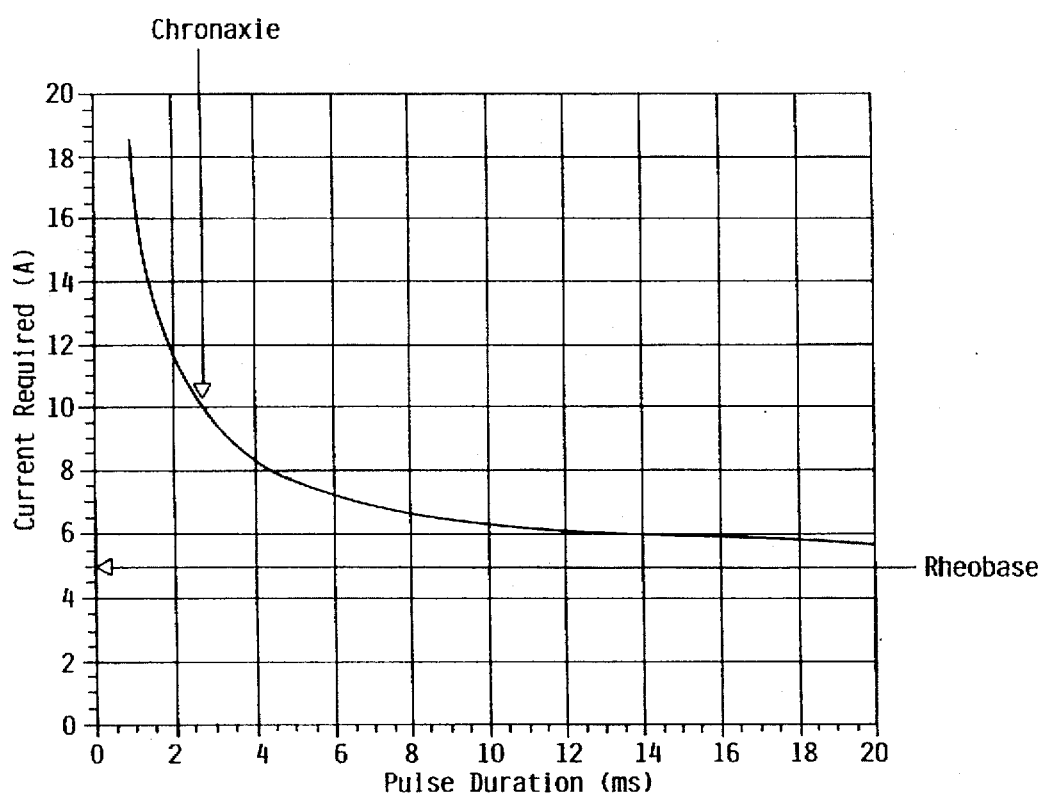
FIG. 1 is a graph showing a typical defibrillation strength-duration curve.

Defibrillation of the human heart is effected by passing a large current through the heart for a time period of several milliseconds. A voltage is generated in the ICD canister and transmitted to the heart through the lead and electrodes. The magnitude of current that is required to successfully defibrillate the heart is related to the pulse width of the shock pulse. This is demonstrated in the "strength-duration" curve (S-D curve) for a typical patient as shown in FIG. 1. The S-D curve shows that in order to successfully defibrillate the exemplary heart with a given set of electrodes, an average current of 6 amps (A.) is required for a pulse width of 13 ms., while an average current of I 1.5 amps is required for a pulse duration of 2 ms.

Since current is caused to flow by a high voltage stored on an energy or charge storage element, typically a capacitor, the impedance of the electrode path must be as low as possible. This is because current is related to voltage and resistance in accordance with Ohm's Law:

$$\text{Current} = \frac{\text{Voltage}}{\text{Resistance}}$$

And, since voltage is determined by the maximum charge that the capacitor can store, the remaining critical variable in determining current flow for a given capacitor is resistance.

It is also the case that the energy of the defibrillation shock pulse sought to be delivered is the primary determinant of the size of the ICD device. This is because the largest component or components of the ICD are the charge storage capacitor(s) and their size is directly proportional to the energy that they must store. Typical ICD devices store approximately 1.77 joules (J) per cubic centimeter (cc) of volume. Thus, the size of the ICD device is a linear function of the energy required for defibrillation. The defibrillation shock energy is given electrically as:

$$\text{Energy} = IVd$$

where I is the current, V is the voltage and d is the duration of the pulse. This formula is exact for rectangular pulses, but is also an accurate approximation when current and voltage vary during the pulse, as is the case with capacitive discharge. In such a case, "V" and "I" are average values. Taking into consideration Ohms Law the energy expression can be rewritten as:

$$E = I(IR)d$$

From this relationship it can be seen that the required energy per pulse is proportional to the electrode resistance. This in turn implies that the size of the ICD device is a linear function of the electrode resistance. Accordingly, in order to accomplish the goal of ICD canister size minimization, while maintaining shock effectiveness, it is of extreme importance to keep the electrode resistance as low as possible.

Figure 2A:
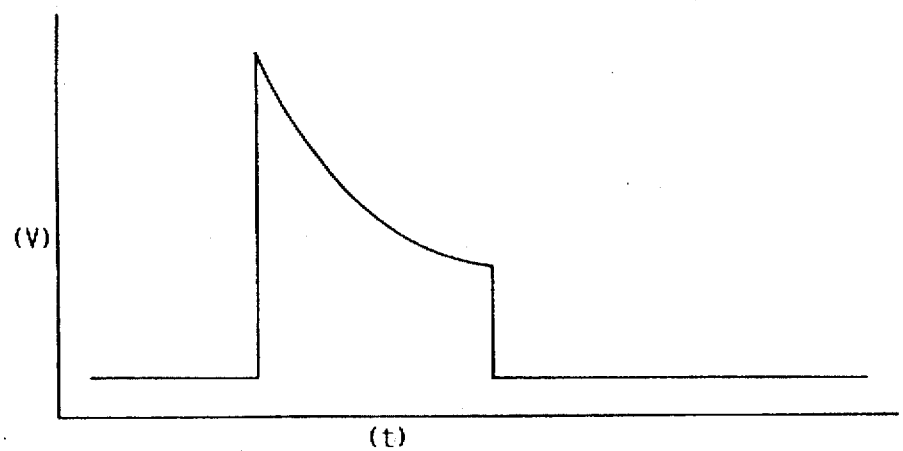
FIGS. 2a and b show typical monophasic and biphasic defibrillation waveforms.
Figure 2B:
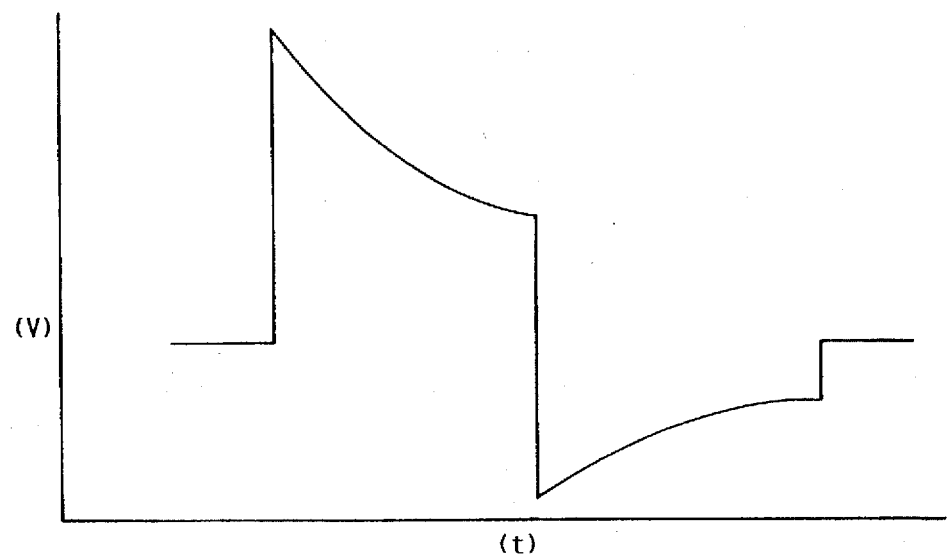

Existing ICD devices and methods deliver either a monophasic or biphasic defibrillation waveform to a patient's heart. The monophasic waveform is shown in FIG. 2a. In this case, an ICD capacitor is charged to a voltage of typically 650–750 V. The capacitor is then allowed to discharge through implanted defibrillation electrodes into the heart for a time period of approximately 6–12 ms. An alternative technique is the delivery of a biphasic waveform. In the case of the biphasic waveform the capacitor is inverted in polarity with an "H-Bridge" switch, for example, to deliver current in a second phase in a polarity opposite to that of its first phase. This is contained for several additional milliseconds at which point the current flow is finally interrupted The biphasic wave is shown in FIG. 2b.

Figure 3:
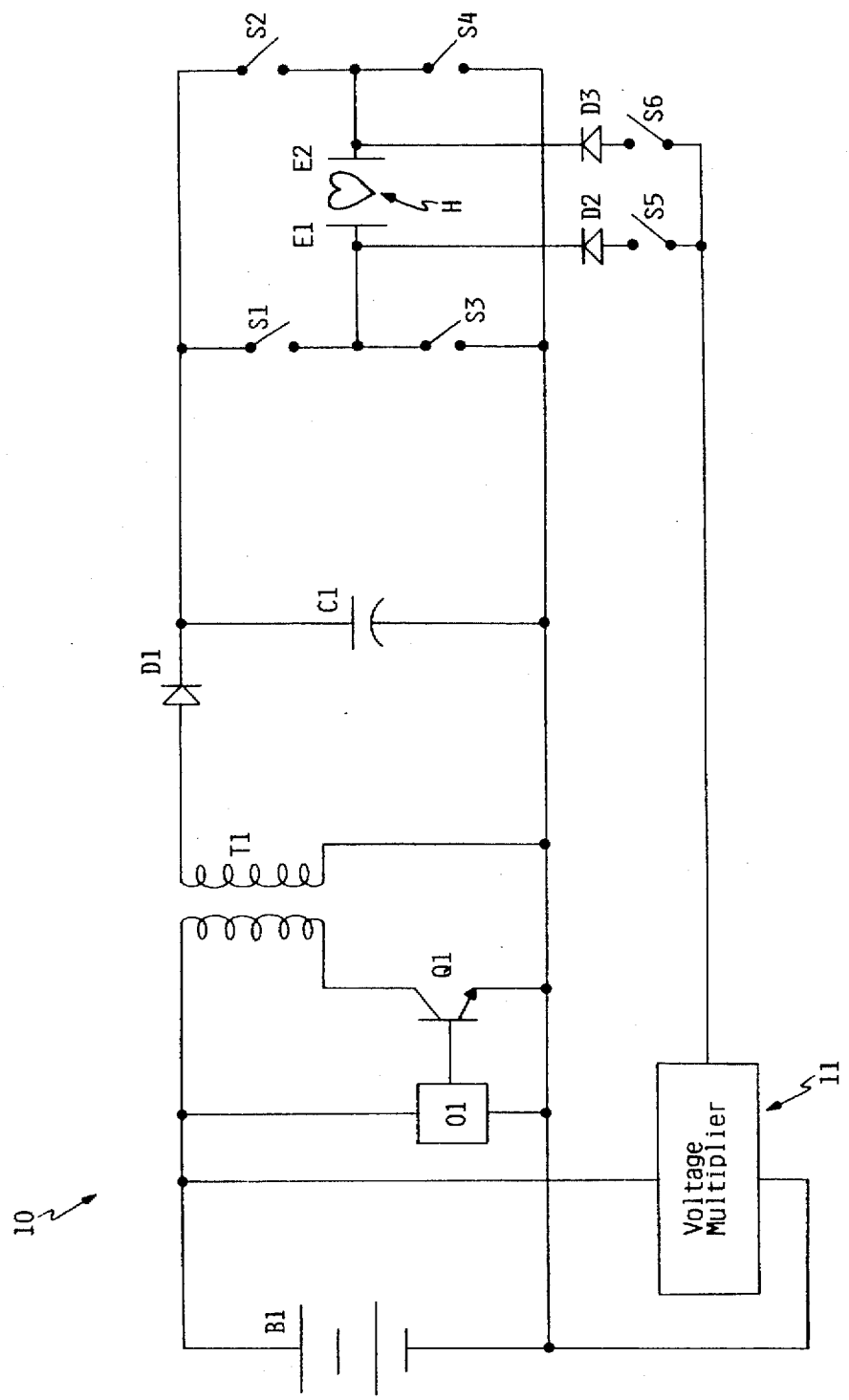
FIG. 3 shows a schematic circuit diagram of the apparatus of the present invention.

Referring to FIG. 3, the apparatus 10 of the present invention basically comprises a battery B1, a transformer T1, a transistor Q1, an oscillator O1, diodes D1, a capacitor C1, and switches S1–4. Electrodes E1 and E2 are preferably catheter-type electrodes known in the art and are inserted into the chambers of the heart. In the alternative, they may be patch style electrodes disposed on the exterior of the heart or the pericardium, or the device housing itself. The battery B1 is used to deliver a current through the primary of transformer T1 at a high frequency generated by transistor Q1 and oscillator O1. This generates a high voltage at the secondary of transformer T1 which is rectified by diode D1 and stored in the main capacitor C1. Preferably, the battery B1 generates a voltage of approximately 6 V. Utilizing the teachings of this invention, a relatively small capacitor of approximately 60–100 microfarads (µF) may be used.

To deliver a monophasic pulse through the heart, switches S1 and S4 are turned on for approximately 3 milliseconds (ms) and then turned off. To deliver a biphasic waveform switches S1 and S4 are turned on for 3 ms, as in the case of a monophasic pulse, and then turned off. Switches S2 and S3 are then immediately turned on for approximately 3 ms to deliver a current in the opposite direction through the heart H.

Importantly, the device 10 further comprises a voltage multiplier 11 which multiplies the battery B1 voltage of approximately 6 V to a level of 12–18 V. Voltage levels up to 50 V may be used, but they require more energy to perform the function more rapidly. This voltage is then delivered to either heart electrode E1 or E2 through additional switches S5 or S6 which are respectively in series with diodes D2 and D3. This voltage is delivered in a pulse of relatively low voltage and of relatively longer duration for back charging purposes as is described further below. All of the switches S1–S6 are communicatively connected to and controlled by a control circuit (not shown) of a design known in the art.

The mode of operation of the apparatus 10 is as follows. After an arrhythmia is detected, the main capacitor C1 is charged up. While the main capacitor C1 is being charged, or during the end of such charging, or after such charging, the voltage multiplier 11 is engaged to generate a voltage of preferably 12–18 V. The switch S6 is turned on to deliver this lower voltage to electrode E2. At the same time, switch S3 is turned on. This allows the flow of the relatively low voltage of 12–18 V from the voltage multiplier 11 through electrode E2, through electrode E1, through switch S3 and back to ground. This will deliver a small current flow through the heart H, with a relatively long pulse duration of approximately 1 second in an opposite polarity to that of the yet-to-come defibrillation pulse. This back charges or precharges the electrodes E1 and E2.

The switches S3 and S6 are then opened and switches S1 and S4 are turned on. This delivers the high voltage, high current, short duration defibrillation shock (approximately 750 V, 5 ms.), through the heart H from electrodes E1 and E2. Importantly, this shock is of opposite polarity to that of the current that was delivered for the back charging of the electrodes E1 and E2. The polarity of the defibrillation pulse is defined as that of the largest voltage phase.

Because the defibrillation shock is delivered with a polarity opposite to that of the back charging flow them is a reduced impedance and more current will pass through the heart H. This results in increased efficiency of defibrillation for a given amount of energy and thus charge storage capacity. And since charge storage capacity is directly related to ICD size, a smaller, more compact ICD 10 is provided. The back charge voltage does not influence cardiac function significantly.

Figure 6:
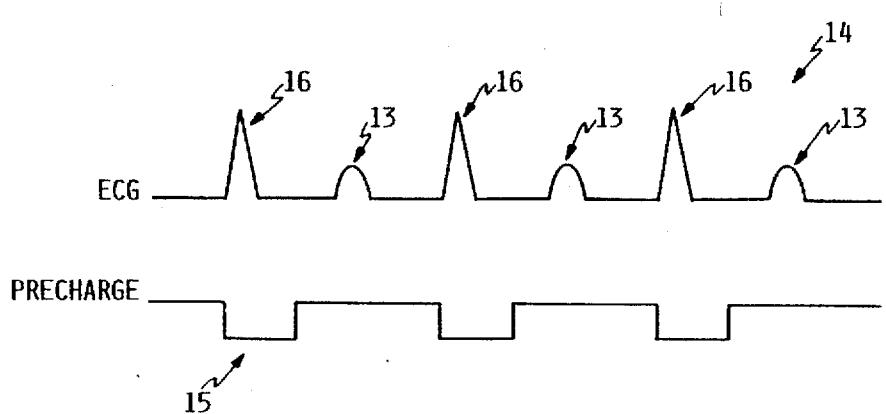
FIG. 6 is a graph showing an exemplary electrogram of cardiac function and an alternative back charge shock sequence.
Figure 7:
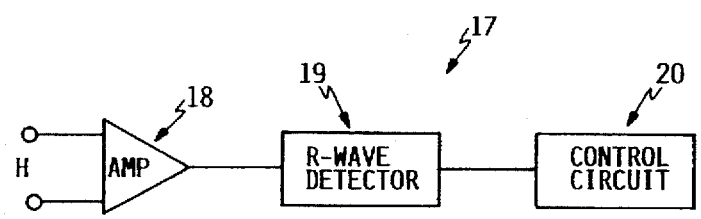
FIG. 7 is an schematic circuit diagram showing an alternative embodiment of the apparatus of this invention.

An alternative embodiment of the apparatus and method of this invention is shown in FIGS. 6 and 7. In a case where a patient is in a ventricular tachycardia (VT) rather than a ventricular fibrillation (VF), the application of a back charging precharging current may cause a ventricular fibrillation by stimulating the heart during the sensitive T-wave region 13 of the electrogram 14. Therefore, in such a case, a back charge current 15 is preferably delivered for only 100 ms after the start of the R-wave region 16 to avoid the T-wave region 13. The apparatus 17 basically comprises, in addition to the elements described above in the main apparatus embodiment 10, an amplifier 18, connected to the heart H, an R-wave detector 19 connected to the amplifier 18, and an ICD control mechanism 20.

Figure 4:
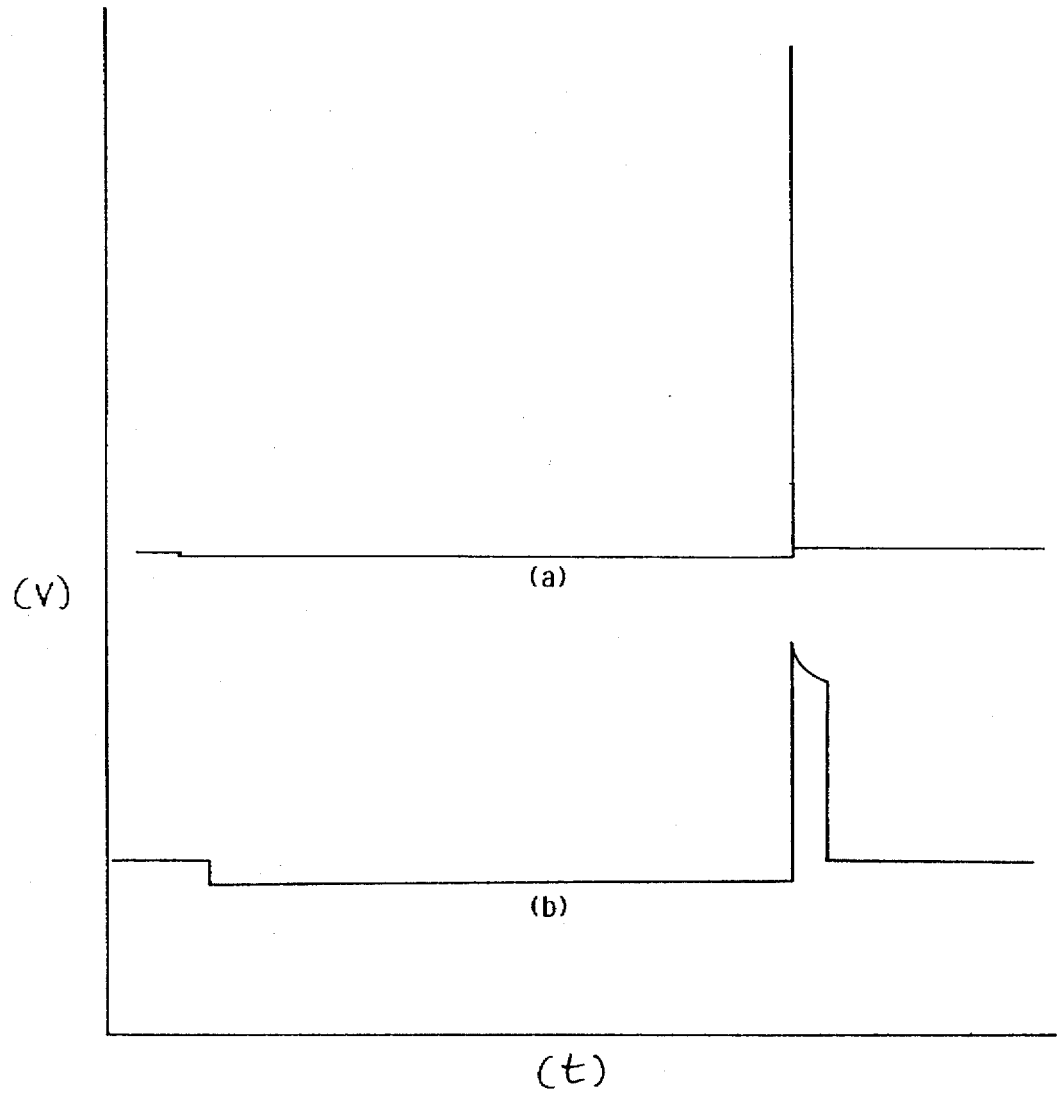
FIG. 4 parts a and b show real scaled and less scaled waveforms, respectively, of a representative defibrillation pulse delivered by the apparatus of the present invention.

Exemplary defibrillation waveforms are shown in FIG. 4 for a monophasic pulse. FIG. 4, part a shows the waveform in approximately real scaling. The long negative low voltage is approximately 1–2 seconds long in duration with a potential of a negative 18 V. The main defibrillation pulse lasts only several milliseconds (i.e., about $1,000^{th}$ as long) but has an amplitude of around 700 V. FIG. 4, part b shows the pulse in a more illustrative and less scaled fashion. Here, the low voltage back charging pulse is shown preceding the main defibrillation pulse.

Figure 5:
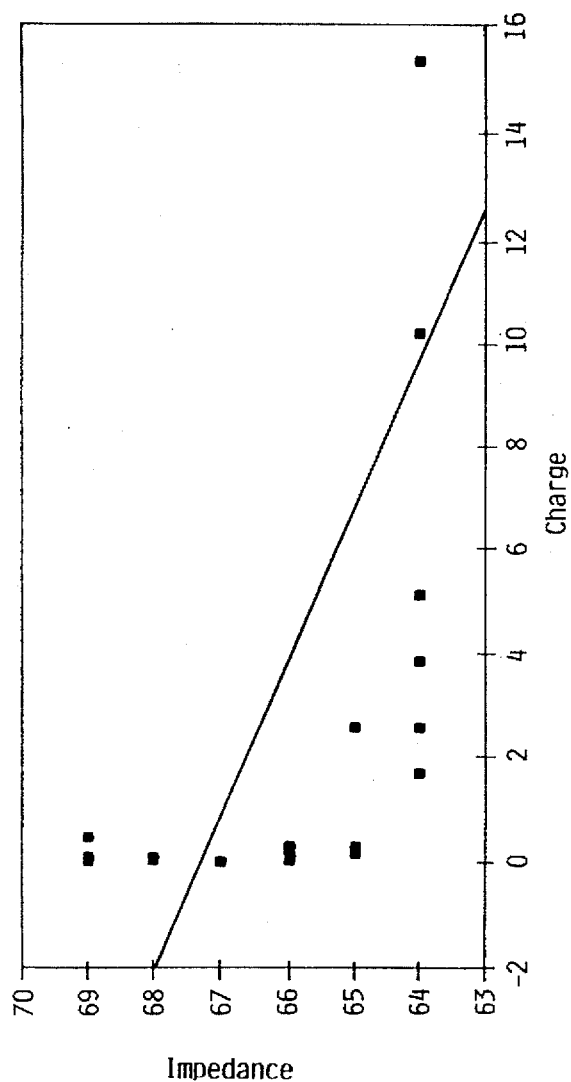
FIG. 5 is a graph showing the effect of shocks delivered by the apparatus of the present invention in terms of impedance and charge (coulombs).

The effects of back charging an electrode pair are shown in the graph of FIG. 5. Here, the back charging is quantified by the charge in coulombs. The coulomb is a unit charge equal to approximately $1/100,000$ of a mole of electrons. It is given electronically as the product of the current and the time. In other words, a current of 1 amp is 1 coulomb flow per second. It should be noted that the impedance in the electrode pair was found to vary from 69 ohms down to 64 ohms with the lower impedance found after a back charging charge of at least 1 coulomb. The example represented in FIG. 5 is based on electrodes constructed of a stainless steel alloy known as MP-35 which is commonly used in defibrillation catheters. The reduction in impedance from 69 to 64 ohms, a reduction of 7 percent, directly translates into a reduction in necessary shock energy of 7 percent. In summary, the delivery of the low voltage, long duration back charging voltage pulse, which is of opposite polarity to that of a subsequently delivered defibrillation pulse, reduces physiological electrode path impedance and increases efficiency of defibrillation for a given mount of energy.

A major mechanism at work in back charging or precharging is the charging of the Helmholtz double layer capacitor. This mechanism basically holds that when an electrode disposed in bodily fluids is charged with a positive voltage it will repel the positively charged sodium ions in a nearby vicinity. The sodium ions cannot move very far away from the electrode as space charge neutrality must be maintained in the fluid in general. This space charge neutrality attempts to force the sodium ions back close to the electrode. The balancing distance is very small and this results in a Helmholtz capacitance. Similarly, the chlorine ions form a Helmholtz capacitance at the negative electrode. In the present invention, the Helmholtz capacitance can be charged by back charging the electrodes. An additional mechanism present, may be an electrochemical reaction at the electrodes, for example, the formation of a titanium oxide.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. An improved implantable cardioverter defibrillator apparatus for producing a capacitive-discharge cardioversion/defibrillation countershock to be delivered through defibrillation electrodes adapted to be implanted in a human patient, the apparatus being a self-contained human implantable device including a pulse-generating capacitor system that stores an electrical charge, a battery system that internally charges the capacitor system, a sensing system that senses cardiac activity of the human patient and detects cardiac dysrythmias, and a control system which, in response to a detected cardiac dysrhythmia, selectively charges and discharges the capacitor system through the defibrillation electrodes to generate the capacitive-discharge cardioversion/defibrillation countershock, the improvement comprising:

means to deliver a back-charging pretreatment pulse to the defibrillation electrodes immediately prior to delivery of the cardioversion/defibrillation countershock, the back-charging pretreatment pulse being a low-energy pulse having a polarity opposite from an initial polarity of the cardioversion/defibrillation countershock such that an inter-electrode impedance of the defibrillation electrodes is reduced and a current of the cardioversion/defibrillation countershock is increased.

2. The apparatus of claim 1 wherein the means to deliver a back-charging pretreatment pulse comprises:

a voltage multiplier connected to the battery system;

a switching system connected between the voltage multiplier and the defibrillation electrodes; and a voltage rectifier connected between the switching system and the defibrillation electrodes.

3. An improved implantable cardioverter defibrillator apparatus for producing a capacitive-discharge cardioversion/defibrillation countershock to be delivered through defibrillation electrodes adapted to be implanted in a human patient, the apparatus being a self-contained human implantable device including a pulse-generating capacitor system that stores an electrical charge, a battery system that internally charges the capacitor system, a sensing system that senses cardiac activity of the human patient and detects cardiac dysrythmias, and a control system which, in response to a detected cardiac dysrhythmia, selectively charges and discharges the capacitor system through the defibrillation electrodes to generate the capacitive-discharge cardioversion/defibrillation countershock, the improvement comprising:

a voltage multiplier connected to the battery system;

a switching system connected between the voltage multiplier and the defibrillation electrodes and connected to the control system; and a voltage rectifier connected between the switching system and the defibrillation electrodes, such that the control system delivers a back-charging pretreatment pulse from the voltage multiplier to the defibrillation electrodes immediately prior to delivery of the cardioversion/defibrillation countershock, the back-charging pretreatment pulse being a low-energy pulse having a polarity opposite from an initial polarity of the cardioversion/defibrillation countershock.

4. An improved implantable cardioverter defibrillator apparatus for producing a capacitive-discharge cardioversion/defibrillation countershock to be delivered through defibrillation electrodes adapted to be implanted in a human patient, the apparatus being a self-contained human implantable device including a pulse-generating capacitor system that stores an electrical charge, a battery system that internally charges the capacitor system, a sensing system that senses cardiac activity of the human patient and detects cardiac dysrythmias, and a control system which, in response to a detected cardiac dysrhythmia, selectively charges and discharges the capacitor system through the defibrillation electrodes to generate the capacitive-discharge cardioversion/defibrillation countershock, the improvement comprising:

means to detect a series of R-waves in the cardiac activity; and means to deliver a series of back-charging pretreatment pulses to the defibrillation electrodes prior to delivery of the cardioversion/defibrillation countershock, each of the series of back-charging pretreatment pulse being a low-energy pulse having a polarity opposite from an initial polarity of the cardioversion/defibrillation countershock and delivered in response to detection of an R-wave such that an inter-electrode impedance of the defibrillation electrodes is reduced and a current of the cardioversion/defibrillation countershock is increased.

5. The apparatus of claim 4 wherein the means to deliver a back-charging pretreatment pulse comprises:

a voltage multiplier connected to the battery system;

a switching system connected between the voltage multiplier and the defibrillation electrodes; and a voltage rectifier connected between the switching system and the defibrillation electrodes.

6. An improved implantable cardioverter defibrillator apparatus for producing a capacitive-discharge cardioversion/defibrillation countershock to be delivered through defibrillation electrodes adapted to be implanted in a human patient, the apparatus being a self-contained human implantable device including a pulse-generating capacitor system that stores an electrical charge, a battery system that internally charges the capacitor system, a sensing system that senses cardiac activity of the human patient and detects cardiac dysrythmias, and a control system which, in response to a detected cardiac dysrhythmia, selectively charges and discharges the capacitor system through the defibrillation electrodes to generate the capacitive-discharge cardioversion/defibrillation countershock, the improvement comprising:

a sense amplifier connected to the sensing system to detect R-waves in the cardiac activity;

a voltage multiplier connected to the battery system;

a switching system connected between the voltage multiplier and the defibrillation electrodes and connected to the control system; and a voltage rectifier connected between the switching system and the defibrillation electrodes, such that the control system delivers a series of back-charging pretreatment pulses from the voltage multiplier to the defibrillation electrodes immediately prior to delivery of the cardioversion/defibrillation countershock, each back-charging pretreatment pulse being a low-energy pulse having a polarity opposite from an initial polarity of the cardioversion/defibrillation countershock and delivered in response to detection of an R-wave.

\* \* \* \* \*

UNITED STATES PATENT AND TRADEMARK OFFICE
CERTIFICATE OF CORRECTION

PATENT NO. : 5,741,303
DATED : Apr.21, 1998
INVENTOR(S) : Mark Kroll, et al

It is certified that error appears in the above-identified patent and that said Letters Patent is hereby corrected as shown below:

On title page, insert item [73] to read:

--Angeion Corporation, Plymouth, Minn.--

Signed and Sealed this

Fourth Day of July, 2000

Attest:

Q. TODD DICKINSON

Attesting Officer

Director of Patents and Trademarks